United States Patent [19]

Holtkamp

[11] Patent Number: Plant 5,540

[45] Date of Patent: Aug. 20, 1985

[54] AFRICAN VIOLET PLANT NAMED CAPRICORN

[75] Inventor: Reinhold Holtkamp, Isselburg, Fed. Rep. of Germany

[73] Assignee: Gessellschaftsvertrag uber die Erfindergemeinschaft "Optimara", Rees Haffen, Fed. Rep. of Germany

[21] Appl. No.: 535,388

[22] Filed: Sep. 23, 1983

[51] Int. Cl.[3] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of African violet named Capricorn characterized by its deep purple-red slightly waved single flowers, variegated leaves having a bright green leaf center, with the leaves being wavy and funnel shaped, and serrated at the edges; very floriferous flowering habit, with 7–9 upright and rigid flower stems being formed, each carrying up to 13 or more single flowers, and by its compact and full flower bouquet positioned centrally above the leaves.

1 Drawing Figure

The present invention comprises a new and distinct cultivar of African violet plant, botanically known as *Saintpaulia ionantha,* and named Capricorn.

The new cultivar was referred to during the breeding and selection process by the designation G 12/93, and is a product of a planned breeding program.

The new cultivar was originated from a cross made in a controlled breeding program in Isselburg, West Germany. The female, or seed parent was a cultivar designated X 4158 single red. The male, or pollen parent was a cultivar named Nashville, disclosed in U.S. Plant Pat. No. 4,533.

The new cultivar Capricorn was discovered and selected by me as a flowering plant within the progeny of the stated cross in a controlled environment in Isselburg, West Germany. Asexual reproduction of the new cultivar by leaf cuttings and by division of shoots, as performed by me at Isselburg, West Germany, has demonstrated that the combination of characteristics as herein disclosed for the new cultivar are firmly fixed and are retained through successive generations of asexual reproduction.

Capricorn has not been observed under all possible environmental conditions. The phenotype may vary significantly with variations in environment such as temperature, light intensity and day length. The following observations, measurements and values describe the new cultivar as grown in Isselburg, West Germany, and Nashville, Tenn., under greenhouse conditions which closely approximate those generally used in commercial practice.

The following traits have been repeatedly observed and are determined to be basic characteristics of Capricorn, which in combination distinguish this African violet as a new and distinct cultivar:

1. Variegated leaves (girl type); serrated, waved and funnel shaped.
2. Very vigorous but compact and uniform growth habit.
3. Center of leaf bright green, providing interesting contrast to medium green leaves.
4. Leaf petioles are short and flexible.
5. 7–9 upright and rigid flower stems, each carrying 13 or more single flowers.
6. Flowers are deep purplish red, slightly waved.

7. Compact flower head positioned centrally above the leaves.

The accompanying photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural light conditions at approximately 2:00 P.M. in early September in Nashville, Tenn. When grown under cooler conditions, the flower color is somewhat more intense.

Botanical classification: *Saintpaulia ionantha,* Ramat. cv CAPRICORN.

Parentage:

*Male parentage.*—Nashville, disclosed in U.S. Plant Pat. No. 4,533

*Female parent.*—X14 4158 single red.

Propagation: The new cultivar holds its distinguishing characteristics through successive propagations by leaf cuttings and by division of shoots.

Plant: From 7 cm. to 9 cm. tall when grown in pots, and approximately 20 cm. in diameter when fully grown.

*Leaves.*—General form: Round, funnel shaped, bright green center, serrated. Diameter: 6–7 cm. Texture: Leather-like velvet; shiny but slightly hairy. Aspect: Shiny, velvet. Veins: Light green to purplish green. Color (upperside): Yellow-green 147A, bright green center, 145 B-C; it is noted that the color in the photograph is much darker than the actual color of the leaves. Color (underside): Green 138C-D. Petiole: Brownish green, hairy, short and flexible.

*Flowers.*—Buds: Ball shaped. Sepals: Spear-shaped, hairy, brownish green when immature. Color: (Mature) red purple 74A-B. Aspect: Velvety.

*Individual flowers.*—Size: 40–45 mm. Color: Upperside: Red-purple 74A-B. Underside: Red-purple 74B-C. Borne: On upright pedicels. Shape: Violet shaped; single, slightly waved. Corolla: Upright. Flowering time: Fully developed flower bouquet appears 8–10 weeks after potting.

*Reproductive organs.*—Anthers: Two cells. Filaments: Light green-hairy, dark purple. Styles: Base of ovary light green and hairy, seed capsule pushed slightly through.

*Roots.*—White when young and active, turning brownish when older.

*Disease resistance.*—Good as known to date.

General observations: Capricorn is a vigorous growing variety, with the centrally located bouquet comprising 7–9 upright stems each of which carries 13 or more deep purple-red single flowers. The girl type leaves are medium to dark green and accentuated with bright green centers, with the leaves being heavily serrated at the edges. Despite its vigorous growth habit, Capricorn is relatively compact and has uniform growth.

I claim:

1. A new and distinct cultivar of African violet named Capricorn, as illustrated and described, and particularly characterized by its deep purple-red slightly waved single flowers, variegated leaves having a bright green leaf center, with the leaves being wavy and funnel shaped, and serrated at the edges; very floriferous flowering habit, with 7–9 upright and rigid flower stems being formed, each carrying up to 13 or more single flowers, and by its compact and full flower bouquet positioned centrally above the leaves.

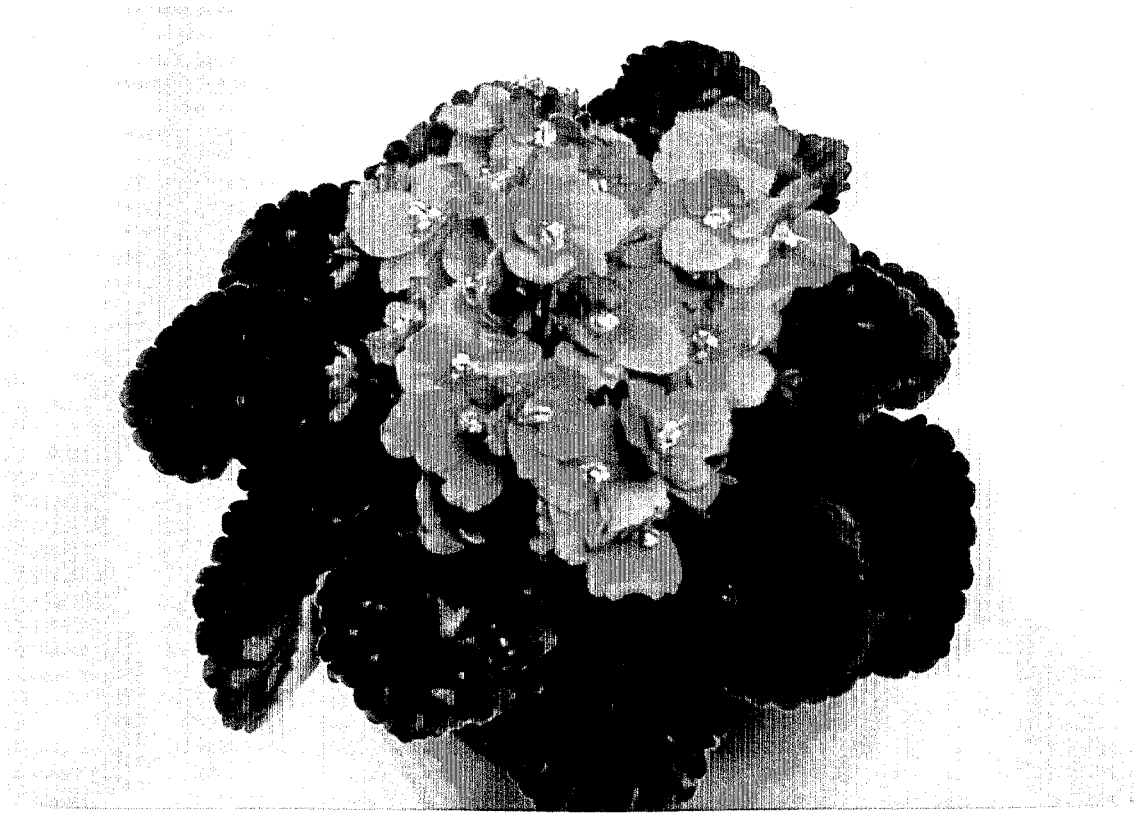

* * * * *